United States Patent [19]
Luce et al.

[11] Patent Number: 5,446,274
[45] Date of Patent: Aug. 29, 1995

[54] INSTRUCTIVE DISPLAY FOR ASSISTING IN CENTERING AN OPTICAL PATH ELEMENT ON A PATH

[75] Inventors: David A. Luce, Clarence Center; Christopher J. Percival, Williamsville, both of N.Y.

[73] Assignee: Leica Inc., Depew, N.Y.

[21] Appl. No.: 199,703

[22] Filed: Feb. 22, 1994

[51] Int. Cl.⁶ .............................................. G01J 1/20
[52] U.S. Cl. ................... 250/206.2; 356/400
[58] Field of Search ............. 250/203.1, 203.3, 203.4, 250/203.6, 208.2, 206.1, 206.2; 356/400, 399, 401

[56] References Cited

U.S. PATENT DOCUMENTS

| | | | |
|---|---|---|---|
| 3,894,230 | 7/1975 | Rorden et al. | 356/400 |
| 3,907,435 | 9/1975 | Roodvoets | 250/203.1 |
| 4,772,123 | 9/1988 | Radner | 356/400 |
| 5,047,609 | 9/1991 | Ekstrand | 356/400 |
| 5,293,221 | 3/1994 | Kitajima et al. | 356/400 |

*Primary Examiner*—Stephone B. Allen
*Attorney, Agent, or Firm*—Bean, Kauffman & Spencer

[57] ABSTRACT

A polar or vector display provides an operator of an optical instrument with a symbolic instruction regarding the direction and amount of motion required to center an optical element on a chosen path.

14 Claims, 3 Drawing Sheets

SPHERE   CYL   AXIS   ADD

INSTRUCTIVE DISPLAY FOR ASSISTING IN CENTERING AN OPTICAL PATH ELEMENT ON A PATH

BACKGROUND OF THE INVENTION

The present invention relates to instructive displays, and more particularly to displays for optical instruments which provide symbolic instruction to assist an operator in centering an optical element on a path.

Many optical instruments, and particularly ophthalmic instruments, require an operator to center an optical element on a path, such as a light path. Lens testing instruments and ophthalmic instruments, such as lensmeters, tonometers, refractors and the like, all require the centering of an optical element on a path. Lensmeters are used to inspect and measure the power of lenses and require centering the lens on a light path, while tonometers and refractors require that the eye be centered with respect to a path. A number of prior art devices utilize a CRT display and require an operator to superimpose two dots and center them with respect to a circle drawn or projected on a screen. U.S. Pat. Nos. 4,511,227, issued Apr. 16, 1985, and 4,705,045, issued Nov. 10, 1987, disclose a tonometer using this type of centering device. Such devices rely heavily on operator skill and intelligence to translate the location and spacing of the two dots into a direction and the amount of motion required to center the object. This heavy reliance on skill and intelligence severely limits the practitioner's choice of operators for performing routine tasks. Other devices have used a CPU to determine the location of the center of a light pattern on a detector and provide an operator with a display of the X-Y location of the component relative to a center path.

BRIEF DESCRIPTION OF THE PRESENT INVENTION

The present invention is directed to instructive displays to assist an operator in centering an optical element, such as a lens, on a light path of an instrument, such as a lensmeter, by displaying symbolic instruction, such as a wedge tapering toward an indicated center, on the display. The wedge taper resembles an arrow directing the operator to move the optical element in a direction toward the center of the light path. The length of the wedge is representative of the distance of the center of the optical element from the center of the light path. As the optical element is moved, the wedge length and/or the location of the wedge changes to reflect the change in position of the optical element relative to the center of the light path. Centering is indicated by some clear representation, such as a flashing starburst or similar type design. Vectors also provide suitable symbolic instruction, since they will assist the operator in knowing the direction of movement required, as well as the amount of movement necessary to center the optical element. One example of a lensmeter which may utilize a display according to the present invention is taught in co-pending application Ser. No. 07/850,890, filed Mar. 13, 1992, now U.S. Pat. No. 5,301,004.

DRAWINGS

FIG. 1 is a graphical representation of a lensmeter;
FIG. 2 illustrates a display according to the present invention showing the various elements;
FIG. 3 shows a display indicating a centered condition;
FIG. 4 is one sequential representation of the change in the wedge displayed as an object is moved toward a centered condition;
FIG. 5 is another sequential representation of the change in the wedge displayed as an object is moved toward a centered condition; and
FIG. 6 is still another representation similar to FIG. 5 using vectors instead of wedges.

DETAILED DESCRIPTION OF THE PRESENT INVENTION

Figure 1:
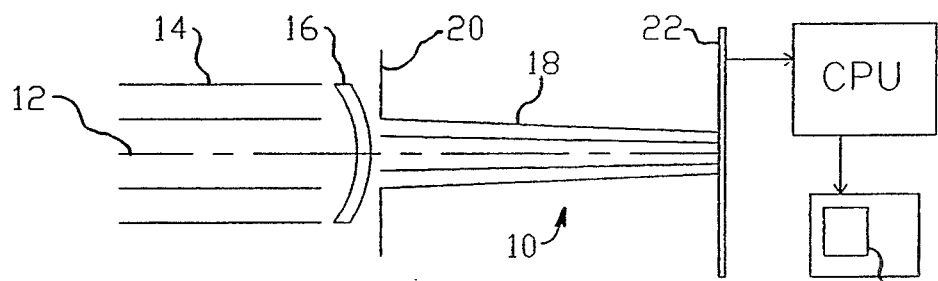

Referring to FIG. 1, lensmeter 10 has path 12 along which collimated light 14 is directed to lens 16 which causes refracted light 18 to pass through occluder 20 that results in a light pattern (not shown) on detector 22. A signal produced by detector 22 is processed by the CPU for driving LCD display 24. While such a display may contain additional information for a lensmeter, it should at least also provide information concerning the sphere, cylinder and axis of a lens. The power of the reading segment and/or axis and amount of prism may also be included. A suitable polar display is Model No. 800 GA available from LXD Inc. of 7650 Pivot Place, Cleveland, Ohio 44146.

Figure 2:
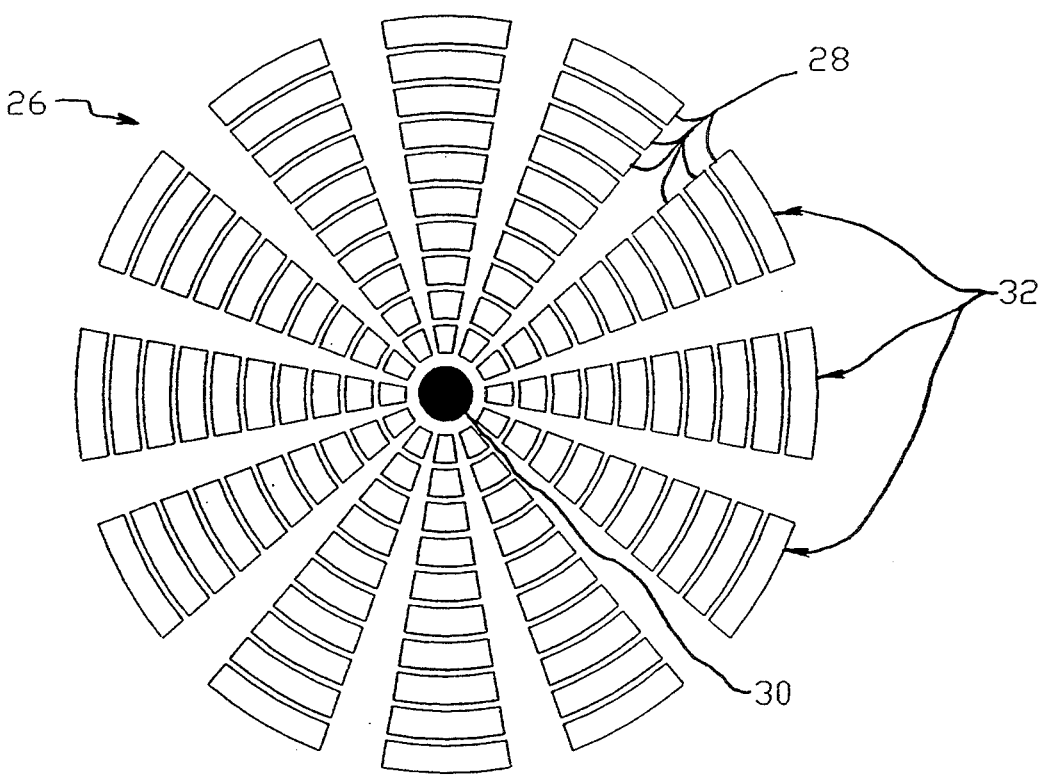
Figure 2:
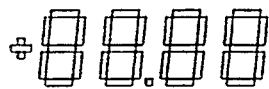
Figure 2:
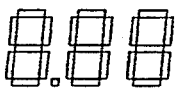
Figure 2:
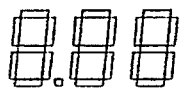
Figure 2:
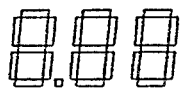

Referring to FIG. 2, polar display 26 has a plurality of arcuate segments 28 arranged in sectors 32 to form wedges tapering toward center 30. Each arcuate segment 28 lies in a specific sector 32 defined by two radii extending from center 30. While the display can contain any reasonable number of sectors and segments in each sector, it has been found convenient to manufacture a display with twelve (12) sectors each having ten (10) segments. In a device such as the 800 GA display, each segment 28 is separately controlled and may be activated by conventional circuitry for LCD displays.

Figure 3:
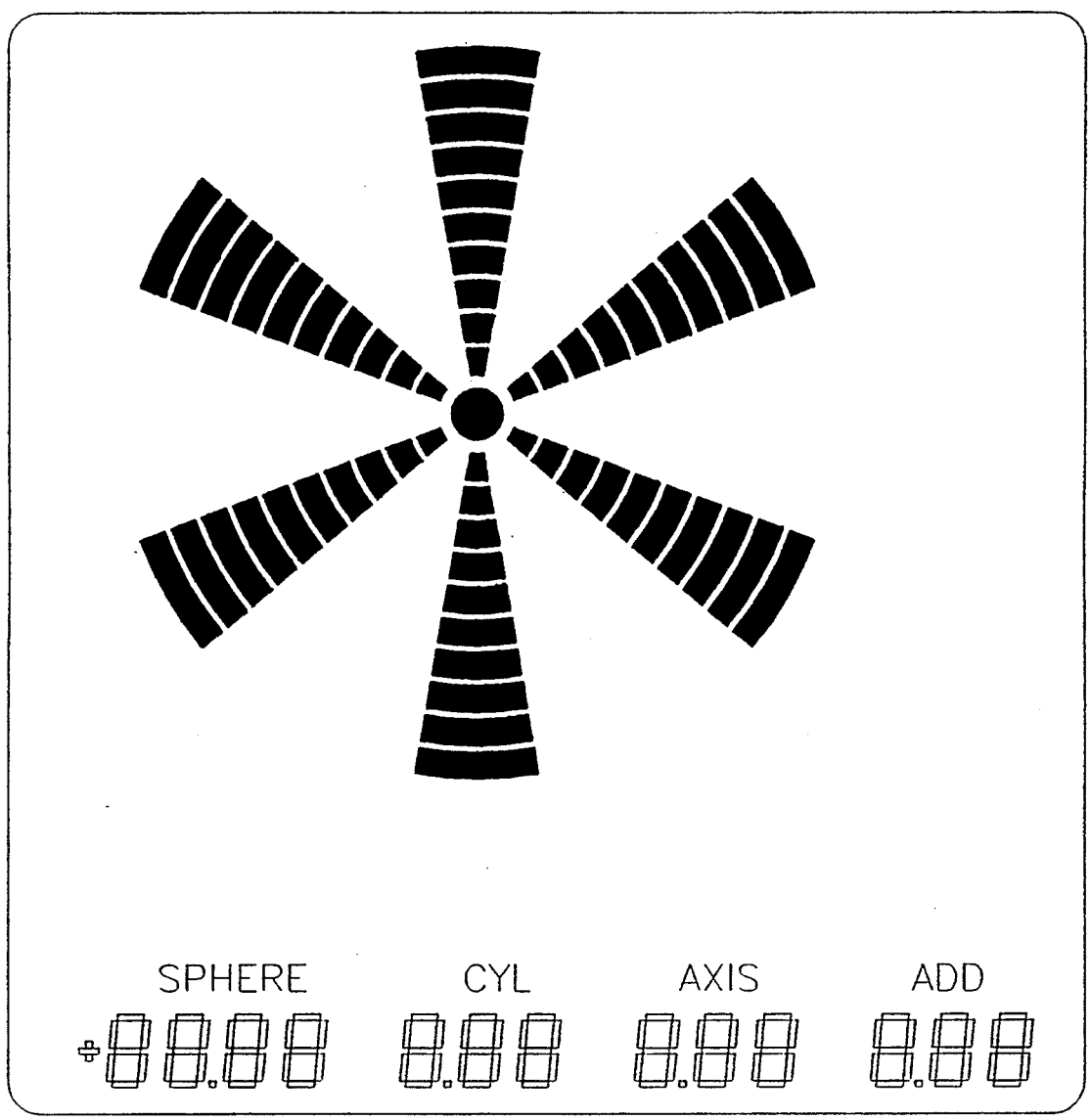

FIG. 3 shows a preferred display for reporting the condition of lens 16 centered on path 12 of lensmeter 10, wherein all segments 28 of alternate sectors 32 are pulsed to provide a flashing starburst type display. The use of a starburst design is optional and any design which notifies the operator that centering has been achieved is suitable.

Figure 4:
Figure 4:
Figure 4:
Figure 4:
Figure 5:
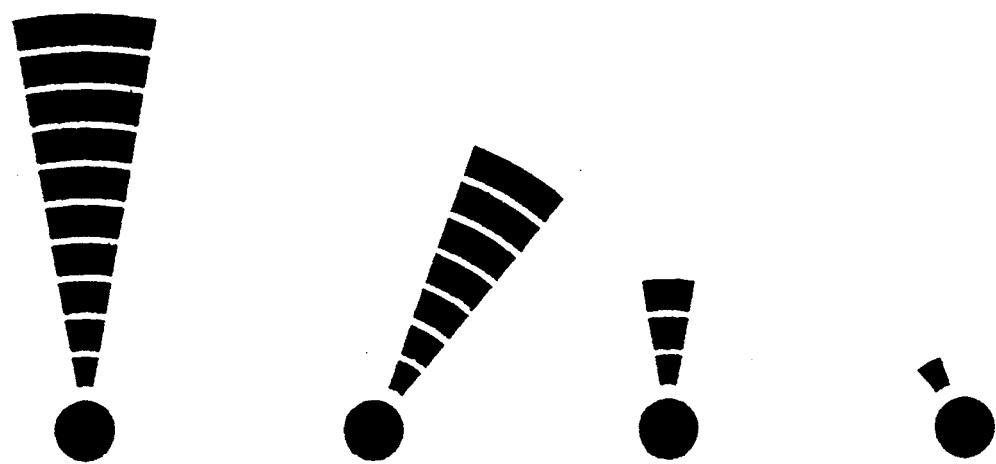
Figure 6:
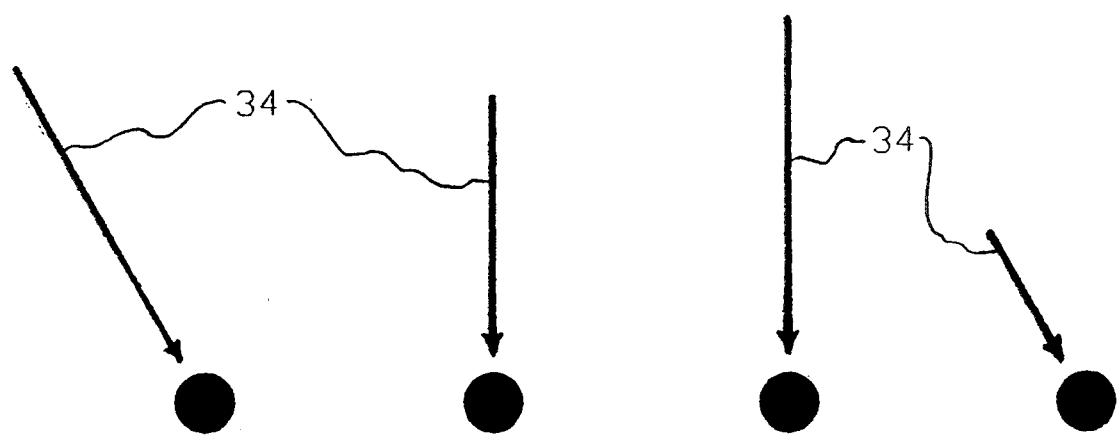

The CPU processes the signal from detector 22 on a continuing basis in order that polar display 26 provides a real time symbolic instruction to the operator regarding the amount and direction of movement required to center lens 16 on path 12 as shown by the sequential representations shown in FIGS. 4 and 5. FIG. 4 illustrates the sequence in which the segments in a particular wedge would be activated as the operator moves lens 16 in a generally straight line toward center 30. FIG. 5 illustrates one symbolic instruction that could result when the operator does not move lens 16 in a generally straight line toward center 30. FIG. 6 is an illustration of a symbolic instruction that could result on a display using vectors 34 when the lens 16 is neither moved in a straight line nor constantly toward center 30.

What is claimed is:
1. A device to assist an operator in centering an optical element on a path which comprises: light sensitive means for generating a signal representing the x-y location of a light pattern received from the optical element, means for determining the center of said pattern, converting said signal to represent the polar location of said center relative to said path, and display means for pro- viding an explicit symbolic instruction representing the direction of movement to center the optical element.

2. The device according to claim 1, wherein said symbolic instruction further represents the amount of movement to center the optical element.

3. The device according to claim 1, wherein said display means includes a plurality of selectively visible angular sectors.

4. The device according to claim 3, wherein said symbolic instruction is a wedge.

5. The device according to claim 2, wherein said symbolic instruction is a vector.

6. The device according to claim 2, wherein said display means includes a plurality of selectively visible angular sectors and selectively visible radial segments.

7. The device according to claim 6, wherein said symbolic instruction is a wedge extending a distance from the center of said display means representative of the distance of said optical element from said path.

8. The device according to claim 1, wherein said display means is a CRT.

9. The device according to claim 1, wherein said display means is an LCD.

10. The device according to claim 5, wherein said display means is a CRT.

11. The device according to claim 6, wherein said display means is an LCD.

12. The invention according to claim 1, wherein said device is a lensmeter.

13. The invention according to claim 7, wherein said device is a lensmeter.

14. The invention according to claim 13, wherein said display means is divided into twelve (12) angular sectors and each angular sector is divided into ten (10) radial segments.

* * * * *